United States Patent [19]

Yoshino

[11] 4,007,738

[45] Feb. 15, 1977

[54] MECHANISM FOR ALLOWING BLOOD BAGS TO COMMUNICATE WITH EACH OTHER

[75] Inventor: Motohiro Yoshino, Fujinomiya, Japan

[73] Assignee: Terumo Corporation, Tokyo, Japan

[22] Filed: July 1, 1975

[21] Appl. No.: 592,171

[30] Foreign Application Priority Data

July 31, 1974 Japan .............................. 49-91544

[52] U.S. Cl. ........................... 128/214 D; 128/247; 128/272; 150/8; 285/260
[51] Int. Cl.² ......................................... A61M 5/14
[58] Field of Search ....... 128/214 R, 214 D, 214 Z, 128/247, 227, 272, DIG. 24; 150/8; 285/3, 4, 260

[56] References Cited

UNITED STATES PATENTS

| | | | |
|---|---|---|---|
| 2,894,510 | 7/1959 | Bellamy | 128/272 |
| 3,110,308 | 11/1963 | Bellamy | 128/214 D |
| 3,648,693 | 3/1972 | Koremura | 128/214 D |
| 3,654,924 | 4/1972 | Wilson et al. | 128/214 D |

*Primary Examiner*—Dalton L. Truluck
*Attorney, Agent, or Firm*—Carroll F. Palmer

[57] ABSTRACT

Disclosed is a mechanism for allowing blood bags to communicate with each other comprising a connection pipe, a connection tube fitted into and bonded to said connection pipe, for connecting a first blood bag to a second blood bag, and a hard plastic-made communication pipe whose one end on the side of said first blood bag is hermetically sealed and the other end of which is fitted into and bonded to said connection tube and which is formed with a cutting-off small thickness section at its intermediate portion. The communication between said first and second blood bags is rendered effective by cutting off said communication pipe at said small thickness section.

5 Claims, 4 Drawing Figures

MECHANISM FOR ALLOWING BLOOD BAGS TO COMMUNICATE WITH EACH OTHER

BACKGROUND OF THE INVENTION

This invention relates to a mechanism for allowing a plurality of blood bags as connected by connection tubes to communicate with each other.

Upon reference to a blood transfusion, it is noted that the age in which whole blood was used to perform a blood transfusion is gone; and presently in order to make an effective use of blood it is separated into components to conduct, for each patient, an appropriate component blood transfusion. Under these circumstances, there has been reported a so-called multiple bag which is integral, closed and sterile-sealed, and may be manipulated wholly from outside itself and in which a plurality of soft plastic-made blood bags are mutually connected by means of connection tubes. This multiple bag is used, for example, to collect whole blood into a blood collecting bag and thereafter subject the collected blood to centrifugation for separating it into two parts—platelet-rich plasma and red blood cell and transfer the upper layer of platelet-rich plasma into a smaller bag through the connection tube, thereby to effect the two part-separation, or is used to subject the platelet-rich plasma to a further centrifugation for separating it into two parts—blood plasma and blood platelet and transfer the upper layer of blood plasma into a still another smaller bag through the connection tube, thereby to effect the three part-separation.

Now, it is necessary to prevent, when the blood is subjected to centrifugation, any inseparated blood from being scattered to the interior of the connection tube. This is because the inseparated blood remaining in the connection tube, upon transfer of, for example, the separated platelet-rich plasma into the smaller bag, is mixed with the plasma causing it to be impure. In the prior art, therefore, a thin film is provided beforehand at that portion of the connection tube interior which is in the proximity of the blood collecting bag, thereby to cut off the communication between the blood collecting bag and the smaller blood bag, and, after the blood has been subjected to centrifugation, this thin film is broken to render said communication effective, thus to transfer the separated plasma into the smaller blood bag. FIG. 1 illustrates this example. A reference numeral 1 denotes the connection tube for connecting the blood collecting bag to the smaller blood bag, said connection tube being partitioned by the thin film 2. Within the connection tube is inserted a breaking needle 3 for breaking the thin film (see FIG. 1A). Upon blood transfer, the breaking needle 3 is moved from outside of the connection pipe 1 to break the thin film, thereby to render the communication between the blood bags effective (see FIG. 1B).

The blood bag-communication mechanism using the above-mentioned thin film has the drawbacks that it presents difficulties in performing its communication operation and is hard for a beginner to handle and further is troublesome to manufacture.

SUMMARY OF THE INVENTION

Accordingly, the object of the invention is to provide a mechanism for allowing blood bags as connected by connection tubes to communicate with each other, which can be handled in a simple manner and manufactured with ease.

According to the invention, there is provided a mechanism for allowing blood bags to communicate with each other comprising:
a connection pipe;
a connection tube for connecting a first blood bag to a second blood bag, the connection tube being fitted into and secured to said connection pipe;
a communication pipe having sealed portion, one end thereof on the side of said second blood bag being fitted into and secured to said connection tube; and
a cutting-off small thickness section formed at said communication pipe between the sealed portion and the secured end thereof;
whereby the communication between said first and second blood bags is rendered effective by cutting off said communication pipe at said small thickness portion.

DETAILED DESCRIPTION OF THE PREFERRED EMBODIMENTS

Hereinafter, an embodiment of the invention is explained with reference to the appended drawing.

Figure 1:
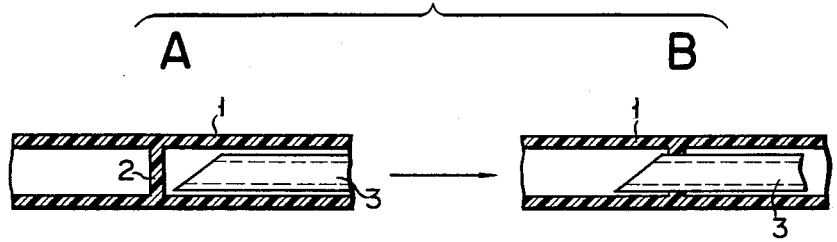
FIG. 1 shows longitudinal sections of a prior art mechanism for allowing blood bags to communicate with each other.
Figure 2:
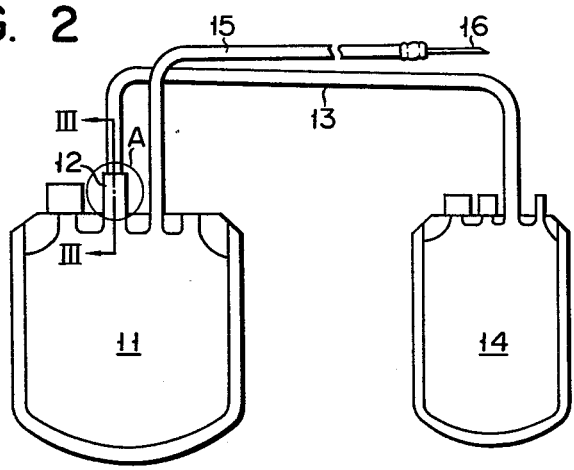
FIG. 2 illustrates a double blood bag.

FIG. 2 illustrates a double blood bag formed of a soft plastic material such as a transparent soft polyvinyl chloride, said double blood bag being used for blood separation into two parts. A blood collecting bag 11 and a smaller blood bag 14 are mutually connected by means of a connection tube 13 made of soft plastic material such as soft polyvinyl chloride, and the communication therebetween is initially rendered ineffective, by a communication mechanism according to the invention, at that portion A of the communication mechanism which is in the neighbourhood of the blood collecting bag. The connection tube 13 is fitted into and secured to a semihard plastic-made connection pipe 12 provided for the blood collecting bag 11.

A blood collecting needle 16 is pierced into the vein of a person whose blood is to be sampled and a proper amount of blood is collected into the blood collecting bag 11 through a blood sampling tube 15. Thereafter, the collected blood is subjected to centrifugation under appropriate conditions. The blood in the bag 11 is separated into two parts—platelet-rich plasma and red blood cell. After the communication between the bag 11 and the smaller bag 14 is rendered effective by means of the communication mechanism according to the invention, the upper layer of platelet-rich plasma is transferred into the smaller bag 14 thus to complete the blood separation.

Figure 3:
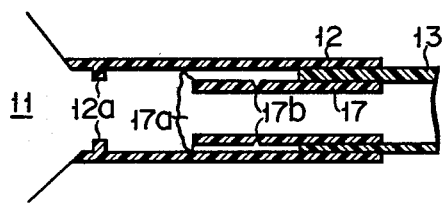
FIG. 3 is a longitudinal sectional view illustrating a mechanism for allowing blood bags to communicate with each other according to the invention.

A detailed description is now made of the blood bag-communication mechanism according to the invention. In FIG. 3, there is illustrated a longitudinal sectional view of the portion A of FIG. 2 taken along the line III—III thereof. For the blood collecting bag 11 is provided the semihard plastic-made connection pipe 12 connected to the connection tube 13. The connection tube 13 is fitted into the connection pipe 12 and secured thereto by using a bonding agent or by high frequency fusion. In this case, however, a short connection tube similar to the tube 13 may be provided on the bag 11, and free end thereof may be fitted into and secured to the pipe 12. A communication pipe 17 is fitted into the connection tube 13 from the blood collecting bag side and is secured thereto by using an appropriate bonding agent or by high frequency fusion. The end portion 17a of the communication pipe 17 on the blood collecting bag side is hermetically sealed by, for example, fusion. Under this condition, the communication between the blood collecting bag 11 and the smaller bag 14 is rendered completely ineffective. Note here that since, in case the even provision of a small thickness section as below described at the pipe 17 fails to permit the pipe 17 to be easily cut off into two pieces—a free piece and a fixed piece, the pipe 17 should be made of hard plastic such as hard polyvinyl chloride.

The intermediate portion of the communication pipe 17 is formed with the small thickness section for cutting off the pipe 17, for example, an annular notch 17b, and when it is desired to render effective the communication between the bag 11 and smaller bag 14, the pipe 17 is manually cut off at this notch 17b from outside of the connection pipe 12. The cutting-off small thickness section may be constituted by such an annular notch as mentioned above but may be constituted also by the one prepared by thinning the large thickness section through, for example, heating and stretching the same. Further, where the small thickness portion is formed of notch, a plurality of notches may be intermittently provided in the same circumference. Further, such notch or notches may be provided either in the outer circumference or in the inner circumference, or both. In this way, the communication between the bag 11 and smaller bag 14 is rendered effective to permit a smooth transfer of the blood from the bag 11 to the smaller bag 14. In order that the free cut-piece of the communication pipe 17 which has been created as a result of cutting-off the pipe 17 can be prevented from being entered into the blood collecting bag 11, an annularly projected portion 12a is provided on the inner circumference of the connection pipe 12. The free cut-piece is interrupted by this annularly projected portion 12a to be prevented from entering the bag 11.

As apparent from the above, the sealed portion of the communication pipe 17 need not be provided at the end 17a, though its provision at the end 17a is preferred. It may be provided at a portion between the notch 17b and the end 17a.

The relations between or among the respective inner and outer diameters of the connection pipe 12, connection tube 13 and communication pipe 17 may be of any kind if the outer diameter of the pipe 17 is smaller than the inner diameter of the pipe 12, and yet have only to be properly determined with the easiness of blood transfer taken into consideration.

Figure 4:
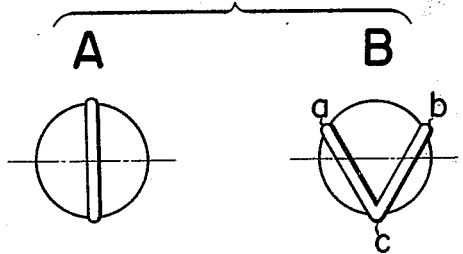
FIG. 4 illustrates the fused conditions of a communication pipe of the mechanism for allowing blood bags to communicate with each other according to the invention.

In performing a hermetical seal of the end portion 17a of the communication pipe 17 by the fusing method, it is desired that the end portion of the fused section is slightly in contact with the inner wall of the connection pipe 12. Bu so doing, the free cut-piece of the pipe 17 is prevented from being again brought into abutment with the fixed piece by being moved owing to the blood flow when blood transfer is carried out. The above-mentioned fusion preferably is conducted as illustrated in FIG. 4 in accordance with the dimension of the inner diameter of the connection pipe 12. FIGS. 4A and B are front views of the end portion 17a of the communication pipe 17, and FIG. 4A illustrates a linearly fused condition in the case where the inner diameter of the connection pipe 12 is relatively large while FIG. 4B illustrates a condition as fused into a V-shape in the case where the inner diameter of the connection pipe 12 is relatively small. By fusing into the V-shape as illustrated in FIG. 4B the terminal parts a, b and c of the end portion 17a are prevented from being strongly pressed against the inner wall of the connection pipe 12 even where the inner diameter thereof is relatively small.

As described above, the blood bag-communication mechanism of the invention is characterized in that the communication pipe formed with the cutting-off small thickness section at its intermediate portion is fitted into and secured to the connection tube for mutual connection of the blood bags, and when the communication between the blood bags is desired to be rendered effective, the communication pipe has only to be cut off at the small thickness section from outside. Accordingly, the blood bag-communication mechanism of the invention is easy to handle and requires no skill as compared with the prior art mechanism wherein the thin film is used to render ineffective the communication between the blood bags and is broken, upon rendering this communication effective, by means of the breaking needle. Further, the securing of the communication pipe to the connection tube has only to be performed by using a bonding agent or by the high frequency fusion, resulting in an easy manufacture of the present mechanism.

What is claimed is:

1. A mechanism for allowing blood bags to communicate with each other, comprising:
    a flexible connection pipe having first and second ends, said first end being connected to and communicated with a first blood bag;
    a connection tube having a first end connected to and communicated with a second blood bag and a second end which is inserted into, and secured to, the second end of said connection pipe;
    a communication pipe of hard plastic material having an open end portion and a sealed end portion, said communication pipe being positioned within said connection pipe; and
    a small thickness section formed in the communication pipe between the sealed end portion and the open end portion, whereby the communication between the first and second blood bags is rendered effective by breaking apart the communication pipe at the small thickness section.

2. The mechanism according to claim 1 wherein the open end of the communication pipe is inserted into, and secured to, the second end of said connection tube.

3. The mechanism according to claim 2 wherein an annular projection is formed on the inner circumference of said connection pipe adjacent said first end so as to prevent any free piece that is formed by breaking of the communication pipe from entering the first blood bag.

4. A mechanism according to claim 2, said communication pipe is formed of hard polyvinyl chloride.

5. A mechanism according to claim 4, wherein said small thickness section formed in said communication pipe is constituted by a notch.

* * * * *